(12) United States Patent
Zhang et al.

(10) Patent No.: US 8,917,811 B2
(45) Date of Patent: Dec. 23, 2014

(54) APPARATUS AND METHOD FOR DYNAMIC CALIBRATION OF SPECTRAL CT WITH ROTATING X-RAY SOURCE AND STATIONARY ENERGY DISCRIMINATING DETECTORS

(71) Applicants: Kabushiki Kaisha Toshiba, Tokyo (JP); Toshiba Medical Systems Corporation, Otawara-shi (JP)

(72) Inventors: Yuexing Zhang, Naperville, IL (US); Xiaolan Wang, Buffalo Grove, IL (US); Yu Zou, Naperville, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 77 days.

(21) Appl. No.: 13/886,645

(22) Filed: May 3, 2013

(65) Prior Publication Data
US 2014/0328451 A1 Nov. 6, 2014

(51) Int. Cl.
*A61B 6/00* (2006.01)
*G01T 7/00* (2006.01)
*G01N 23/04* (2006.01)

(52) U.S. Cl.
CPC .............. *G01T 7/005* (2013.01); *G01N 23/046* (2013.01)

USPC .................................. 378/5; 378/16; 378/207

(58) Field of Classification Search
CPC ........ A61B 6/032; A61B 6/482; A61B 6/483; A61B 6/4241; A61B 6/4275; A61B 6/4035; A61B 6/585; G06T 11/005; G01N 23/046; G01N 23/083; G21K 1/10
USPC ...................... 378/4, 5, 10, 16, 156, 159, 207
See application file for complete search history.

(56) References Cited

U.S. PATENT DOCUMENTS 6,950,493 B2 * 9/2005 Besson ........................... 378/16

FOREIGN PATENT DOCUMENTS

JP 2000-060841 A 2/2000

\* cited by examiner

*Primary Examiner* — Jurie Yun
(74) *Attorney, Agent, or Firm* — Oblon, Spivak, McClelland, Maier & Neustadt, L.L.P.

(57) ABSTRACT

An apparatus and method for dynamically calibrating a computed-tomography (CT) scanner that includes a rotating X-ray source and a plurality of stationary energy-discriminating detectors configured to capture incident X-ray photons emitted from the X-ray source. A bowtie filter with a unique geometry and material composition is used to generate reference beams of a desired intensity. The apparatus includes a processor that is configured to remove a scattering background based on data obtained from the reference beams and compute a change in a predetermined calibration function.

10 Claims, 6 Drawing Sheets

APPARATUS AND METHOD FOR DYNAMIC CALIBRATION OF SPECTRAL CT WITH ROTATING X-RAY SOURCE AND STATIONARY ENERGY DISCRIMINATING DETECTORS

FIELD

Embodiments disclosed herein generally relate to computed tomography (CT) imaging. In particular, embodiments disclosed herein relate to an apparatus and an associated method for dynamic calibration in spectral CT that comprises a rotating X-ray source and a plurality of stationary energy discriminating detectors.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low-energy X-ray from the generator, the details of the geometry and characteristics of the detector and the capacity of the acquisition system are all elements that affect how the actual reconstruction is performed.

Further, the measured X-ray intensity on a detector may include both scattering photons and primary photons. Thus, the images reconstructed from scattering (contaminated intensities) may contain scattering artifacts.

In one of many possible geometries, the X-ray source on top of the graph shown in FIG. 1 is emitting a X-ray beam forming a fan, traversing the object. While a wide range of values can exist, typically, the distance "C" is around 100 cm, "B" is around 60 cm, and "A" is around 40 cm. The principle of tomography requires that each point of the object is traversed by a collection of rays covering at least 180 degrees. Mathematical considerations show that the tomographic conditions are met when a scan of 180 degrees plus the fan angle is performed. In addition to the details of the scanner geometry and the detector behavior, the very nature of the X-ray interaction with the matter it traverses makes the problem more complex and requires another layer of correction and compensation.

For example, scattering is one of the major sources of discrepancy between the expected attenuation behavior and the measured data from a scanner without an anti-scatter grid or with a non-perfect anti-scatter grid. The naïve assumption that all the measured photons originate directly from the X-ray source is not exactly true. X-ray photons can be diverted from their original course in a purely elastic collision (Rayleigh scattering) or in a more complex inelastic collision (Compton scattering) in which both direction and energy are affected.

Several systems have been proposed to address scattering contamination. For example, most modern commercial scanners include an "anti-scatter" filter. This device is a collimation system exploiting the fact that all scattered photons will be diverted from their original path and will therefore enter the detector at a different angle from the photons coming directly from the X-ray tube, which is typically a small (e.g., less than one millimeter wide) point that is on the order of one meter away.

Energy discriminating detectors such as CdTe/CdZnTe-based photon-counting detectors may further experience changes in their responses to incident X-ray flux and energy spectrum due to effects such as temperature-drift, hysteresis associated with X-ray exposure and crystal polarization.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1:
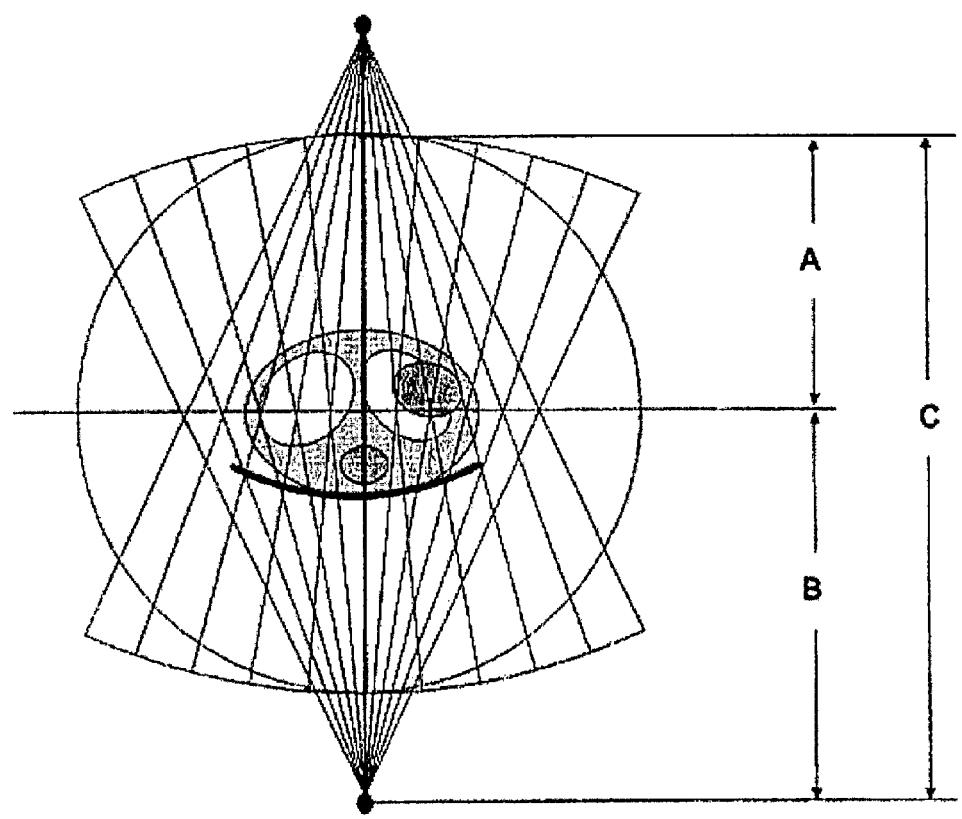
FIG. 1 illustrates an X-ray source emitting an X-ray beam forming a fan, traversing an object.

Embodiments disclosed herein relate to an apparatus and method for dynamic calibration of spectral CT equipped with a rotating X-ray source and stationary energy discriminating detectors.

In one embodiment, there is provided a computed-tomography (CT) apparatus, comprising: (1) a rotating X-ray source; (2) a plurality of stationary energy-discriminating detectors configured to capture incident X-ray photons emitted from the X-ray source; (3) a bowtie filter configured to generate reference beams of respective desired intensities outside a scan field of view; and (4) a processor configured to obtain reference count rates corresponding to the reference beams incident on a detector outside the scan field of view, and update a calibration function based on the obtained reference count rates at the detector, wherein the updated calibration function is used to determine X-ray intensities from scan count rates obtained at the detector when the detector is within the scan field of view.

In one embodiment, there is provided a method for calibrating a computed-tomography (CT) scanner, comprising: (1) generating reference beams of respective desired intensities outside a scan field of view; (2) capturing incident X-ray photons at an energy-discriminating detector; (3) obtaining reference count rates corresponding to the reference beams incident on the detector when the detector is outside the scan field of view; (4) updating a calibration function based on the obtained reference count rates at the detector, wherein the updated calibration function is used to determine X-ray intensities from scan count rates obtained at the detector when the detector is within the scan field of view.

In another embodiment of the disclosure is provided a non-transitory computer readable medium having stored thereon a program that when executed by a computer, causes the computer to perform the steps of: (1) generating reference beams of respective desired intensities outside a scan field of view; (2) capturing incident X-ray photons at an energy-discriminating detector; (3) obtaining reference count rates corresponding to the reference beams incident on the detector when the detector is outside the scan field of view; (4) updating a calibration function based on the obtained reference count rates at the detector, wherein the updated calibration function is used to determine X-ray intensities from scan count rates obtained at the detector when the detector is within the scan field of view.

Bowtie filters are commonly employed in third-generation CT scanners to minimize the radiation dose by reducing intensity variations across detector elements in the presence of patient anatomy. Such filtration modifies a number of X-ray beam properties (effective energy, flux, first and second order statistics), making them non-uniform across the fan beam field of view. When bowtie filters are properly implemented, they provide reduction of patient exposure with minimal image degradation. Accordingly, it is an objective of the present disclosure to provide an apparatus and an associated method for dynamically calibrating the apparatus in order to obtain an accurate detector response according to measured count rate and incident spectrum.

Figure 2:
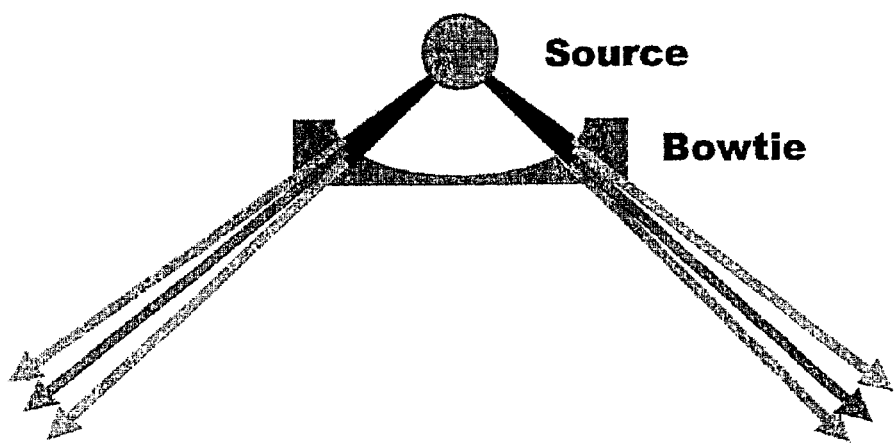
FIG. 2 illustrates a leading edge and a trailing edge reference beam.

In one embodiment, as shown in FIG. 2, by designing a bowtie filter with a unique geometry and material composition, X-rays having a specific intensity and spectrum, at the edge of the source fan and outside the scan field of view are obtained for fourth-generation energy-discriminating detectors. Energy-discriminating detectors experience changes in their response to incident X-ray flux and energy spectrum due to effects such as temperature-drift, hysteresis associated with X-ray exposure and crystal polarization. Hence, a bowtie filter with a specific geometry can be used in the dynamic calibration of a CT apparatus. In what follows, we explain in detail the process of dynamically calibrating a CT apparatus with reference to FIGS. 2-5.

For a spectral CT detector, the incident X-ray spectra can be divided into energy bins represented as $E_i$, and the incident X-ray of intensity $\vec{I}$ can be represented as follows:

$$\vec{I} = \begin{pmatrix} I(E_1) \\ I(E_2) \\ \vdots \\ I(E_N) \end{pmatrix} \quad (1)$$

where $(E_1, E_2, \ldots, E_N)$ represents N energy bins.

A spectral detector responds to incident X-ray of intensity $\vec{I}$ and generates output count rates (e.g., counts per view) for all energy bins. The count rate of an energy bin can be represented as $n(E_i)$, and the count rate generated by a detector can be represented as $$\vec{n} = \begin{pmatrix} n(E_1) \\ n(E_2) \\ \vdots \\ n(E_N) \end{pmatrix} \quad (2)$$

The response function of the detector can be determined from a calibration and/or modeling function ($f_c$) and be represented as:

$$\vec{n}_c = f_c(\vec{I}) \quad (3)$$

Note that $\vec{n}_c = f_c(\vec{I})$ is the "true" response from the detector. The inverse of the function $f_c$ provides the "true" incident X-ray intensity based on the count rate reading from the detector, i.e., $\vec{I} = f_c^{-1}(\vec{n}_c)$. Further, as mentioned previously, due to factors such as temperature variations and hysteresis, the detector response deviates from the calibrated function $f_c$, and become $f_s$ during scans. Correspondingly, the detector output can be represented as follows:

$$\vec{n}_s = f_s(\vec{I}) \quad (4)$$

Note that the function $f_s$ is unknown and changes from scan to scan, and needs to be corrected by employing a dynamic calibration function.

To correct for the deviation, the detector responses are measured with reference beams at the leading and trailing edges of the source fan beam, outside the scan field of view (SFOV), as shown in FIG. 2. Note that the reference primary beam intensities and spectra are known, while the scattering is unknown. Scattering can be removed if the two adjacent reference beams differ considerably, while the scattering background is considered to be constant.

Figure 3:
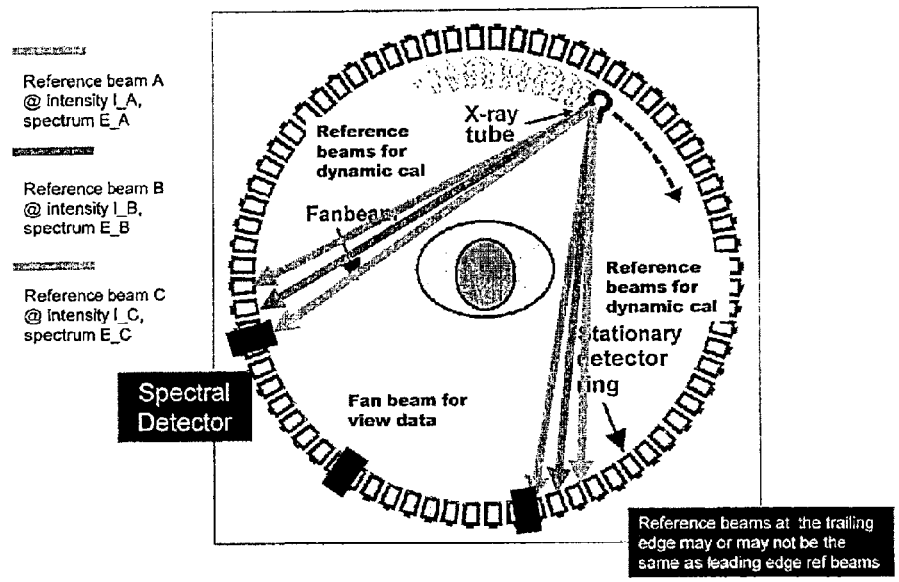
FIG. 3 illustrates a CT apparatus including a rotating X-ray source and a ring of stationary detectors.
Figure 4:
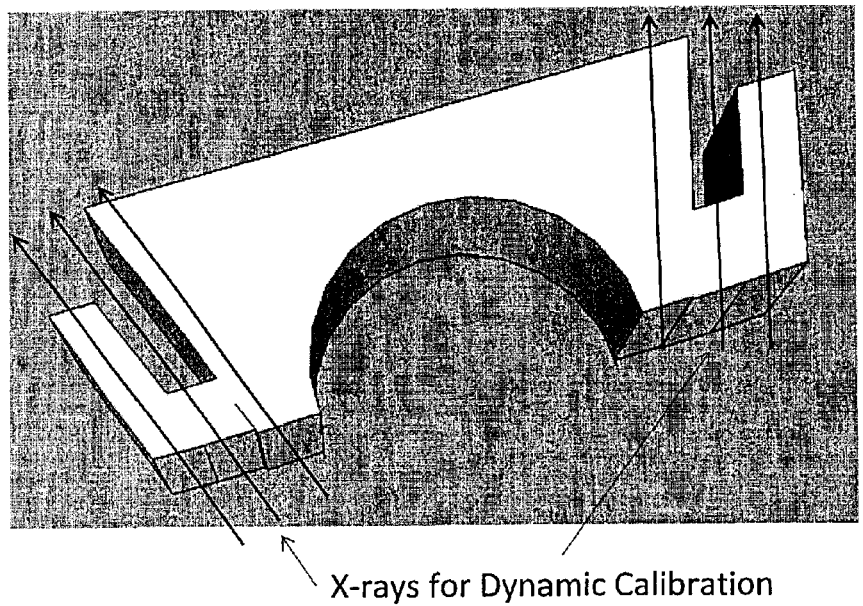
FIG. 4 is a non limiting example depicting the geometry of a bowtie filter.

As shown in FIG. 3, the CT apparatus in the present disclosure is a fourth-generation CT that includes a rotating X-ray source and a ring of stationary detectors. The reference beams generated at the leading edge and the trailing edge of the source fan are of a certain specific intensity and spectrum, and lie outside the SFOV. The reference beams can be obtained by designing a bowtie filter with a unique geometry and material composition, as shown in FIG. 4.

A bowtie filter is used as a mechanism for performing pre-patient filtration. Specifically, the cross-section of a human body is of an elliptical form, which leads to larger X-ray attenuation at the center of the body and smaller attenuation near the periphery. Therefore, the X-ray intensity detected at the detector has a large dynamic range, thereby posing challenges for the data acquisition system. The bowtie filter with its unique geometry, reduces the dynamic range and improves dosage efficiency. The bowtie filter is thicker at the edges and thinner at the center. Further, note that the bowtie filter can even include an air channel to obtain an X-ray of a specific intensity.

We now outline an example depicting the process of dynamic calibration performed by a fourth-generation CT apparatus according to one embodiment. Consider, for example, adjacent reference beams A and B with intensities of $\vec{I}^A$ and $\vec{I}^B$ respectively. The intensity of the beams can be represented as follows:

$$\vec{I}^A = \vec{I}_{primary}^A + \vec{I}_{scattering}^A \quad (5)$$

and $$\vec{I}^B = \vec{I}_{primary}^B + \vec{I}_{scattering}^B \quad (6)$$

Note that $\vec{I}_{primary}^A$ and $\vec{I}_{primary}^B$ are known by design, whereas $\vec{I}_{scattering}^A$ and $\vec{I}_{scattering}^B$ are the intensities due to the scattering effect. In this model, since we consider that the scattering backgrounds are the same, we have $\vec{I}_{scattering}^A \approx \vec{I}_{scattering}^B$. Therefore, subtracting equation (6) from equation (5) we have:

$$\vec{I}^A - \vec{I}^B \approx \vec{I}_{primary}^A - \vec{I}_{primary}^B \quad (7)$$

In an extreme case, the bowtie filter is designed such that $\vec{I}_{primary}^B \approx 0$. In this way, $\vec{I}^A - \vec{I}^B \approx \vec{I}_{primary}^A$. The dynamic calibration operates in ranges where $f_c(\vec{I})$ and $f_s(\vec{I})$ can be approximated as linear functions. For reference beams A and B, the measured count rates can be respectively expressed as $$\vec{n}_s^A = f_s(\vec{I}^A) \text{ and } \vec{n}_s^B = f_s(\vec{I}^B). \quad (8)$$

Hence, on subtracting the count rates of beams A and B we get, $$\Delta \vec{n}_s^{A-B} = \vec{n}_s^A - \vec{n}_s^B = f_s(\vec{I}_{primary}^A - \vec{I}_{primary}^B) \quad (9)$$

Note that the same holds true for other adjacent reference beams in both the leading edge and the trailing edge. However, due to an insufficient number of reference beams and measurements, it is possible that one may not be able to fully determine the function $f_s$. Hence, as an alternative, the function $f_s$ can be approximated as follows:

$$f_s = f_c + \delta f \quad (10)$$

where $\delta f$ is a variation of a small amount in the calibration function and contains fewer variables that can be determined with a limited number of measurements. Upon calculating $\delta f$ (and therefore, $f_s$), the updated response function to obtain the "true" count rates for measurements within the SFOV for the same scan can be used.

Assume that the operator $f$ can be parameterized by a few parameters, namely, $$f_s = f(\vec{\alpha}^{(s)}) \quad (11a)$$

$$f_c = f(\vec{\alpha}^{(c)}) \quad (11b)$$

where $$\vec{\alpha} = (\alpha_1, \alpha_2, \alpha_3, \ldots \alpha_K)^T \quad (12)$$

indicates the parameters. With a first-order approximation, $\delta f$ can be determined as follows:

$$\delta f = f(\vec{\alpha}^{(s)}) - f(\vec{\alpha}^{(c)}) \approx \sum_{k=1}^{K} (\alpha_k^{(s)} - \alpha_k^{(c)}) \left[ \frac{\partial f(\vec{\alpha})}{\partial \alpha_k} \right]_{\vec{\alpha} = \vec{\alpha}^{(c)}}, \quad (13)$$

Note that parameters $\alpha_k^{(s)}$ can be determined from the data of the leading edge beam to the trailing edge beam.

Then, the intensity within the SFOV can be calculated as follows:

$$\vec{I}_{view\ data} = f_s^{-1}(\vec{n}_{view\ data}) \quad (14)$$

Note, however, that if $\delta f$ changes with time from the leading edge beam to the trailing edge beam during a scan, one may determine $\delta f(t)$ at both the leading edge and the trailing edge, and then use interpolated values for view data correction.

Figure 5:
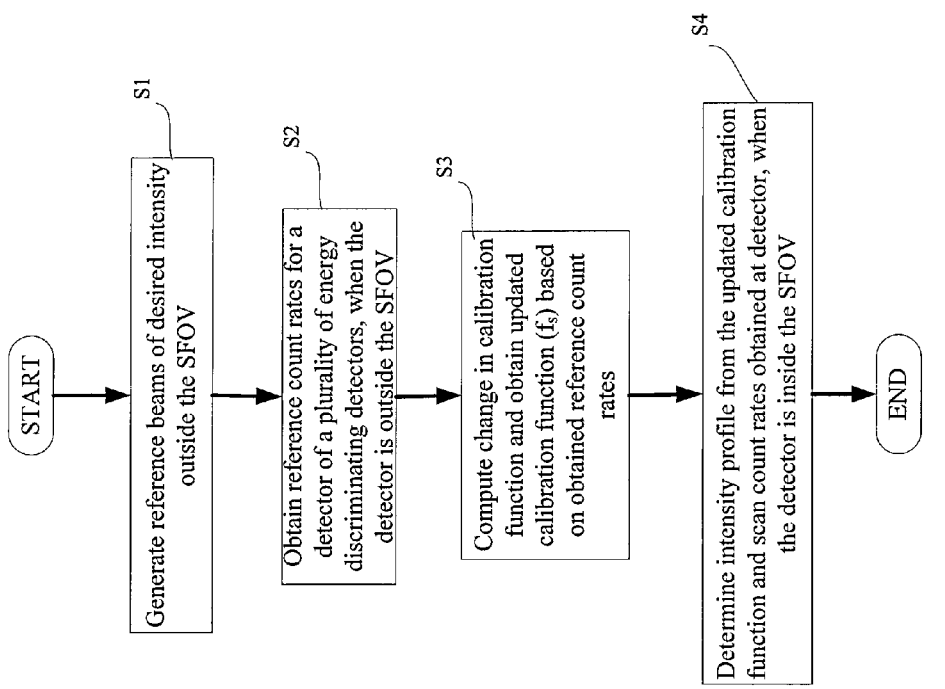
FIG. 5 is a flowchart illustrating the steps taken for dynamic calibration of the CT apparatus.

FIG. 5 depicts the steps undertaken by a controller to dynamically calibrate the CT apparatus.

In Step S1, a bowtie filter of specific geometry and material composition is used to generate reference beams of desired intensities outside the scanned field of view. The bowtie filter generates variations in beam intensities and spectra for the adjacent beams. Further, note that the reference beams are used in the dynamic calibration of the CT apparatus.

In Step S2, data is collected from the adjacent reference beams that are incident on a detector. Specifically, reference count rates at a detector that is outside the SFOV is obtained. Note that by knowing the primary intensities of the reference beams, scattering can be corrected, as shown in equations (5) to (7).

In Step S3, a change in the predetermined calibration function is computed, as described by equations (8) and (9). Further, from equations (4), (10) and (13), the detector output can be computed by $$\vec{n}_s = f_c(\vec{I}) + \sum_{k=1}^{K} (\alpha_k^{(s)} - \alpha_k^{(c)}) \left[ \frac{\partial f(\vec{\alpha})}{\partial \alpha_k} \right]_{\vec{\alpha} = \vec{\alpha}^{(c)}} (\vec{I}). \quad (15)$$

Further, note that for the leading edge beam to the trailing edge beam during a scan, the incident count $\vec{I}$ in each energy bins are known. Hence, from the measured count, $\vec{n}_s$, the corrected parameters $\alpha_k^{(s)}$ (and thus the corrected $f_s$) can be obtained from (15). Specifically, the updated calibration function $f_s$, is obtained based on the reference count rates detected in Step S2.

Further, in Step S4, the intensity profile at a detector that is within the SFOV is determined based on a scan count rate measured by the detector when it is within the SFOV, and the updated calibration function $f_s$ that is computed in Step S3. Note that this intensity profile at the detector can be computed by using Equation 14.

Figure 6:
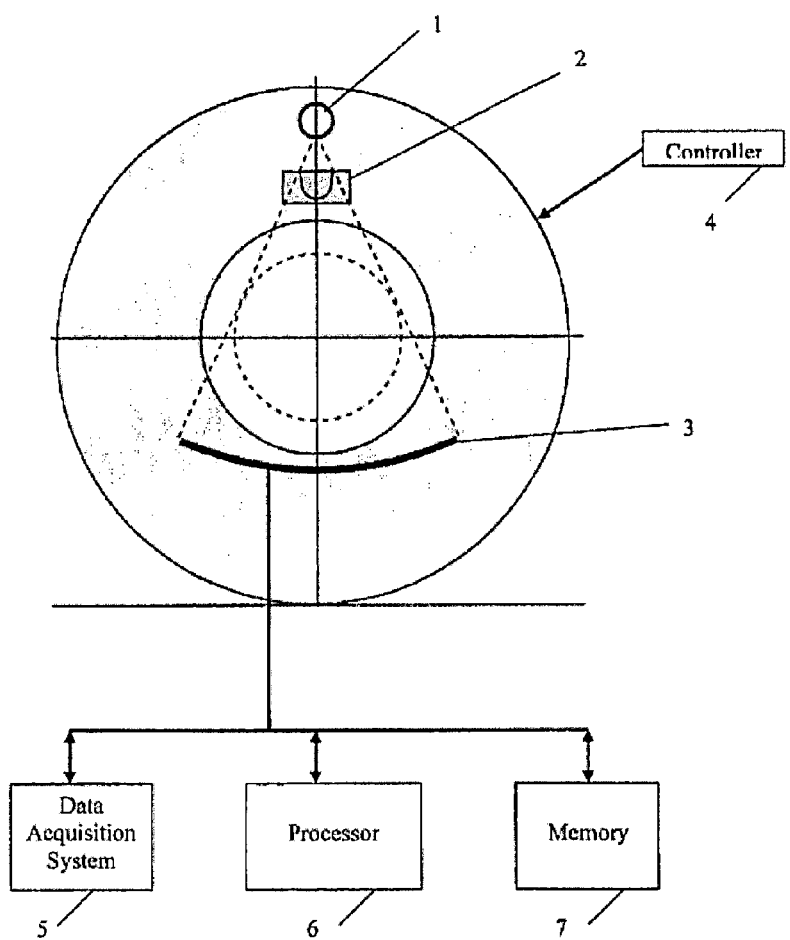
FIG. 6 is a diagram of a mechanically simplified CT apparatus.

FIG. 6 illustrates the basic structure of a CT apparatus that includes the detectors described herein. The CT apparatus of FIG. 6 includes an X-ray tube 1, filters and collimators 2, and detector 3. The CT apparatus will also include additional mechanical and electrical components such as a gantry motor and a controller 4 to control the rotation of the gantry, control the X-ray source, and control a patient bed. The CT apparatus also includes a data acquisition system 5 and a (reconstruction) processor 6 to generate CT images based on the projection data acquired by the data acquisition system. The processor and data acquisition system make use of a memory 7, which is configured to store, e.g., data obtained from the detector and reconstructed images.

The processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

The processor includes a reconstruction processor, which is configured to generate CT images from the new data. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only and are not intended to limit the scope of the inventions. Indeed the novel methods and systems described herein may be embodied in a variety of other forms. Furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, comprising:
    a rotating X-ray source;
    a plurality of stationary energy-discriminating detectors configured to capture incident X-ray photons emitted from the X-ray source;
    a bowtie filter configured to generate reference beams of respective desired intensities outside a scan field of view; and
    a processor configured to
        obtain reference count rates corresponding to the reference beams incident on a detector outside the scan field of view, and
        update a calibration function based on the obtained reference count rates at the detector, wherein the updated calibration function is used to determine X-ray intensities from scan count rates obtained at the detector when the detector is within the scan field of view.

2. The CT apparatus of claim 1, wherein the X-ray source and the bowtie filter generate
    the reference beams including a leading reference beam and a trailing reference beam.

3. The CT apparatus of claim 2, wherein both the leading reference beam and the trailing
    reference beam are used to update the calibration function.

4. The CT apparatus of claim 1, wherein the processor is configured to update a respective calibration function for each detector of the plurality of energy-discriminating detectors.

5. The CT apparatus of claim 1, wherein a change in the calibration function is time-dependent.

6. The CT apparatus of claim 1, wherein the bowtie filter includes an air channel to create
    an X-ray of desired intensity.

7. The CT apparatus of claim 1, wherein the processor is further configured to perform scattering correction based on data collected when the reference beams are incident on the detector.

8. The CT apparatus of claim 1, wherein the processor is configured to update the calibration function by calculating a change in the calibration function using a first-order approximation.

9. A method for calibrating a computed-tomography (CT) scanner, comprising:
    generating reference beams of respective desired intensities outside a scan field of view;
    capturing incident X-ray photons at an energy-discriminating detector;
    obtaining reference count rates corresponding to the reference beams incident on the detector when the detector is outside the scan field of view;
    updating a calibration function based on the obtained reference count rates at the detector, wherein the updated calibration function is used to determine X-ray intensities from scan count rates obtained at the detector when the detector is within the scan field of view.

10. A non-transitory computer readable medium having stored thereon a program that when executed by a computer, causes a computed-tomography apparatus to perform the steps of:
    generating reference beams of respective desired intensities outside a scan field of view;
    capturing incident X-ray photons at an energy-discriminating detector;
    obtaining reference count rates corresponding to the reference beams incident on the detector when the detector is outside the scan field of view;
    updating a calibration function based on the obtained reference count rates at the detector, wherein the updated calibration function is used to determine X-ray intensities from scan count rates obtained at the detector when the detector is within the scan field of view.

* * * * *